United States Patent [19]

Winchell et al.

[11] 4,046,276

[45] Sept. 6, 1977

[54] PORT PROTECTOR CAP FOR A CONTAINER

[75] Inventors: David A. Winchell, Twin Lakes, Wis.; Joe A. Miller, Lake Zurich, Ill.; Jerry D. Martin, Kenosha, Wis.

[73] Assignee: Baxter Travenol Laboratories, Inc., Deerfield, Ill.

[21] Appl. No.: 705,211

[22] Filed: July 14, 1976

[51] Int. Cl.$^2$ ............................................. B65D 41/20
[52] U.S. Cl. .................................. 215/250; 128/272; 150/8; 215/305; 215/320
[58] Field of Search ............... 128/214 D, 272; 53/14, 53/41; 215/247, 248, 250, 253, 260, 262, 269, 270, 271, 316, 317, 320, 354, 228, 305; 150/8

[56] References Cited

U.S. PATENT DOCUMENTS

| 2,266,270 | 12/1941 | Roth | 215/317 |
|---|---|---|---|
| 2,634,014 | 4/1953 | Kimber | 215/271 X |
| 2,717,728 | 9/1955 | Gray | 215/354 X |
| 2,723,041 | 11/1955 | Hart-Still | 215/270 |
| 2,953,272 | 9/1960 | Mumford | 215/260 |
| 3,030,955 | 4/1962 | Gossett | 128/272 |
| 3,152,711 | 10/1964 | Mumford | 215/271 |
| 3,244,308 | 4/1966 | Esposito | 215/270 |
| 3,746,001 | 7/1973 | Ralston | 150/8 X |

*Primary Examiner*—Donald F. Norton
*Attorney, Agent, or Firm*—Eugene M. Cummings; Paul C. Flattery; John P. Kirby, Jr.

[57] ABSTRACT

A protector cap for establishing a sterile seal over a port having a puncturable section in a container wall and a cylindrical neck portion projecting from the periphery of the wall section. The cap comprises a molded housing having a ring-shaped recess for sealingly engaging the neck member and a chamber formed at least in part within a compressible handle portion. The handle portion is compressed prior to inserting the cap on the neck portion of the port and is subsequently released to establish a partial vacuum in the chamber. The partial vacuum assists in retaining the protector cap in position and prevents trapped air from forcing the cap off during subsequent heat-sterilization of the container.

8 Claims, 5 Drawing Figures

U.S. Patent  Sept. 6, 1977  4,046,276
FIG. 1
FIG. 2
FIG. 3
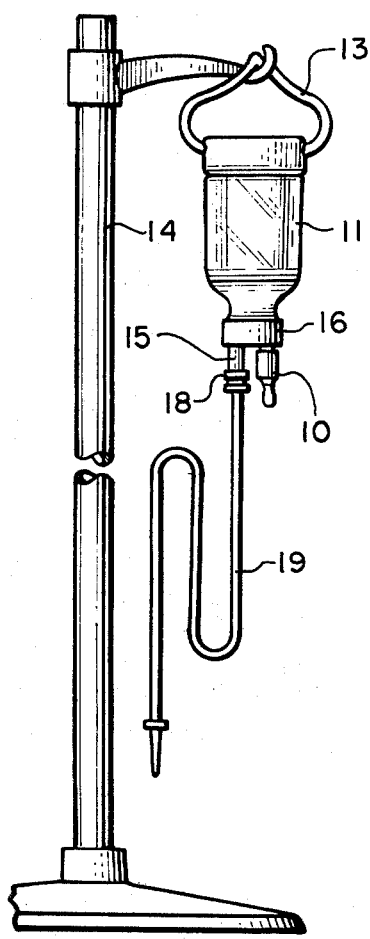
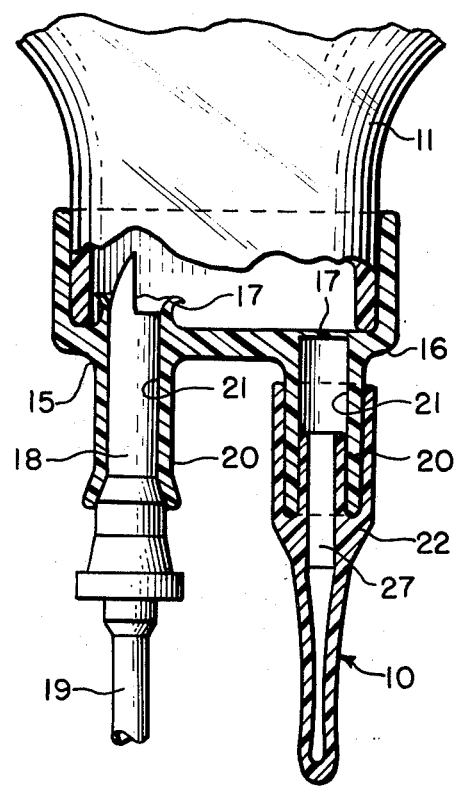
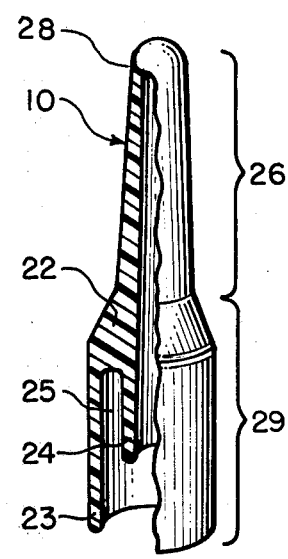
FIG. 5
FIG. 4
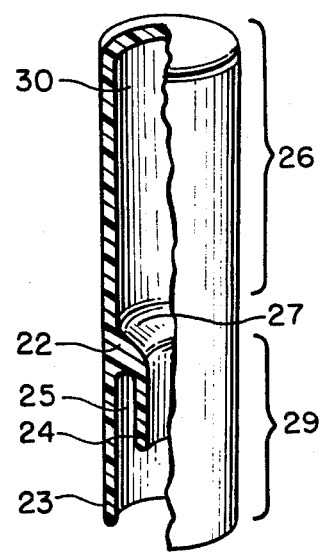
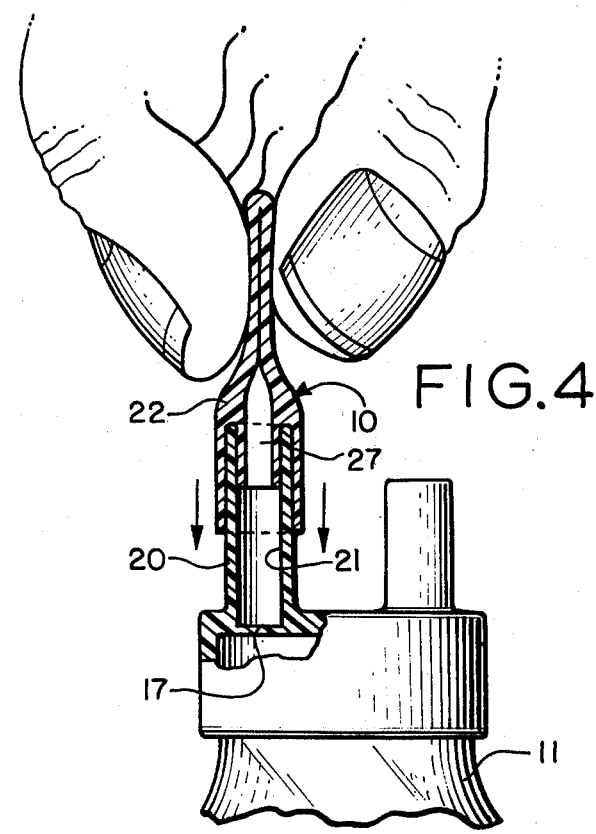

PORT PROTECTOR CAP FOR A CONTAINER

BACKGROUND OF THE INVENTION

The present invention is directed generally to a cap assembly, and more particularly to a protector cap for providing a positive sterility seal over the port of a pharmaceutical container.

Fluids intended for intravenous administration, such as nutrient solutions and blood, must be sterile at the time of use to avoid the danger of introducing harmful agents into the body. This requires not only that the container and its contents be in a sterile sealed condition at the time of receipt by the user, but also that no contamination of the contents occur when the container is opened by a physician or medical technician prior to use. The problem of maintaining sterility is particularly acute at the port of the container where the container wall is punctured by the point of the cannula of an administration set or other flow system to allow removal of the fluid, since the danger exists that contamination accumulated on the container housing during transport or storage may be introduced by the cannula into the container.

To guard against this it has become common practice to provide a protective cap over the container port, which ordinarily consists of a thin puncturable wall portion in the housing through which the cannula is inserted, and a cylindrical molded neck portion protruding from around the wall portion on which the cap is seated. The neck portion includes a central passageway and provides protection for the wall portion as well as a seat for the cap. The cap remains in place until the time of use, when it is removed from the neck portion and the cannula is inserted through the underlying wall portion to withdraw the fluid in the container for use.

One problem with this arrangement had been the necessity of tightly affixing the protective cap to prevent its falling off during transit or storage. This has made the caps difficult to remove, particularly under the emergency conditions and in the unfavorable environments where patients must often be treated. Even the most effective seal arrangement becomes unsatisfactory and potentially dangerous when it is excessively difficult or time-consuming to remove, since attention may have to be diverted from the patient undergoing treatment.

Another problem with such cap assemblies has been the impossibility of determining whether the sterile condition in the container port has in fact been maintained. Should the protective cap become loose or fall off in transit, and be subsequently replaced or tightened, the danger exists that the neck portion of the port may harbor contamination which can be carried by the cannula into the solution being adminstered. Another problem with prior art protector caps is that as they were initially installed on a container neck portion they caused air to be trapped and compressed within the neck portion. When the container was subsequently heat-sterilized in an autoclave, the compressed air expanded and, being trapped, loosened or blew off the caps.

Accordingly, the present invention is generally directed to a new and improved protector cap for maintaining a seal at the port of a fluid container.

The invention is further directed to a new and improved cap for maintaining a vacuum over the puncturable membrane portion of the port of a fluid container.

The invention is further directed to a new and improved protector cap for the port of a fluid container which is not subject to being forced off by trapped air during subsequent heat-sterilization.

SUMMARY OF THE INVENTION

The invention is directed to a protector cap for a fluid container of the type having a port having a puncturable wall portion and a cylindrical neck portion protruding from the periphery of the wall portion. The cap comprises a housing which includes means defining a first ring-shaped recess at one end of the cap for sealably receiving the neck portion, and means defining a chamber opening at the same end and having a user-deformable wall whereby the volume thereof can be reduced prior to installation of the cap on the port to establish at least a partial vacuum in conjunction with the wall and neck portions of the port.

The invention is further directed to a port assembly for a fluid container. The port assembly comprises a puncturable wall portion in the container, a cylindrical neck portion projecting outwardly from the periphery of the wall portion, and a protector cap which includes a housing having means defining a first ring-shaped recess at one end of the cap for sealable receiving the neck portion of the port, and means defining a chamber opening at the same end and having a user-deformable wall whereby the volume thereof can be reduced prior to installation of the cap on the port to establish at least a partial vacuum in conjunction with the wall and neck portions.

The invention is further directed to the method of establishing by means of a resilient compressible protector cap a sterility-protecting seal over the port of a fluid container of the type having a puncturable wall portion and a cylindrical neck portion projecting from the periphery of said wall portion. The method comprises the steps of compressing the protector cap, sealingly engaging the protector cap to the neck portion while maintaining the cap in compression to form a sealed chamber therebetween, and releasing the cap to establish a partial vacuum within the chamber.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a two-port fluid container and associated intravenous administration set illustrating the port assembly and protector cap of the invention.

FIG. 2 is an enlarged cross-sectional view of the two ports of the container of FIG. 1 showing one port being opened by means of a cannula and the other port being maintained sealed by means of a protector cap constructed in accordance with the invention.

FIG. 3 is a perspective view partially in cross-section of the protector cap.

FIG. 4 is a front elevational view partially in cross-section showing the protector cap being installed on the port of a fluid container.

FIG. 5 is a perspective view partially in cross-section of an alternate construction for the protector cap.

DESCRIPTION OF THE PREFERRED EMBODIMENT

Referring to the Figures, and particularly to FIG. 1, a protector cap 10 constructed in accordance with the invention is intended for use in conjunction with a fluid container 11 of the type commonly utilized for containing fluids to be administered intravenously into the body. The container may be manufactured of glass material in the form shown, or may be manufactured from a flexible plastic material, such as vinyl plastic, which may be folded about itself and sealed along its edges to form a bag. The container may be supported by suitable means such as a hanger 13 and conventional support stand 14.

At its bottom end the container 11 may have one or more ports through which fluid may be extracted. In the illustrated container two such ports are provided, indicated generally as 15 and 16. Each of these ports has associated with it a wall section 17 of reduced thickness which may be punctured by insertion of a cannula to allow fluid to be withdrawn from the container. This is illustrated in conjunction with port 15, a hollow-cored cannula 18 having been inserted through the wall section to establish fluid communication with an intravenous administration set 19.

To prevent contamination from entering container 11 when the wall section 17 is punctured, each of the ports includes a projecting cylindrical neck portion 20 within which an axially-aligned bore 21 having an inside diameter substantially corresponding to the outside diameter of the cannula is provided. To prevent contamination from collecting on the inside surface of the bore 21 during storage and transit the neck portion is covered by the protector cap 10. This cap is installed during the initial filling of the container prior to sterilization. Cap 10 remains installed to protect the bore against contamination until immediately prior to use.

In accordance with the invention, the protector cap 10 is made of a relatively flexible non porous material, such as a natural or synthetic rubber. Where the container and its contents are sterilized by heat, cap 10 should be of a material which does not deform by heat at the sterilization temperatures.

Protector cap 10 includes at its open end an outer sleeve portion 23 and an inner sleeve portion 24. The sleeve portions are concentrically spaced and of sufficient length to form a ring-shaped recess 25 in which the cylindrically-shaped neck portions 20 of the container ports can be received. The inner sleeve portion 24 may be shorter than the outer sleeve portion 23 as shown for more convenient insertion over neck 20, or may be of the same length for greater sealing effect. In either case, the sleeve portions 23 and 24 are joined at one end and connected to a handle portion 26 located generally at the closed end of the cap. The handle portion 26 includes an axially-aligned generally bore-shaped chamber 27 which extends along the inside surface of sleeve portion 24 to the open end of the protector cap.

The wall 28 of handle portion 26 is relatively thin and flexible so that it can be compressed by the user to reduce the volume of chamber 27, as shown in FIG. 4. This has the effect of expelling air which would ordinarily be contained in the chamber, so that when the protector cap is ultimately pushed over the neck portion 20 of the container port as shown in FIG. 4, a partial vacuum is developed within the chamber when the walls are released and attempt to assume their original shape.

While it is contemplated that sleeve portions 23 and 24 may extend the entire length of the protector cap to the closed end of handle portion 26, it is preferable that the sleeve portions terminate at the handle portion as shown in the Figures so that only the single wall 28 need be compressed. To this end, the sleeve portions 23 and 24 may be formed within a base portion 29 (FIG. 3) of the protector cap having a larger outside diameter than the handle portion 26. Alternatively, chamber 27 may include a bulbous portion 30 of increased diameter within handle portion 26 as shown in FIG. 5, and the base and handle portions may be of the same diameter. This arrangement has the advantage of allowing a larger reduction to be made in the volume of chamber 27 when the handle portion 26 is compressed.

In use, the handle portion 26 of the protector cap 10 is first compressed and then inserted, either manually or by means of appropriate machinery, over the projecting neck portion 20 of a container port. When the protector cap is seated with the projecting edges of neck portion 20 abutting the closed end of recess 25, the compressive force on the handle portion 26 is released and the wall 28 attempts to return to its original non-compressed shape. The resulting partial vacuum formed within chamber 27 coupled with a slight interference fit holds the protector cap in position. Since the air trapped in the chamber can freely expand, it will not force the cap out of its seated position during subsequent heat-sterilization.

In removing the protector cap, the user grasps the cap by handle portion 26 and pulls the cap away from the container port. If the seal is still intact, a "pop" sound will be heard as the seal is broken, thus assuring the user of the integrity of the seal. Once the cap has been removed a cannula may be inserted through wall portion 17, the bore 21 being dimensioned to maintain a tight contamination-free seal.

Thus, an improved protector cap for an intravenous fluid container has been realized which provides improved sealing and is more convenient to install and remove. Since the protector cap does not require a large interference fit, it may be easily installed by means of automatic assembly apparatus. Furthermore, since pressure within the cap is decreased instead of increased, unlike prior art designs, there is no tendency for the cap to be forced off the container by expansion of trapped air during subsequent autoclaving, and a definite pop sound is produced as the cap is removed to assure the user of the integrity of the seal.

It will be appreciated that other constructions are possible for the protector cap. For example, the handle portion 26 can be enlarged to a diameter greater than the base portion 29 to provide a greater compressible volume in chamber 27 than that provided with the alternate embodiment shown in FIG. 5.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A protector cap for a fluid container of the type having a port comprising a puncturable wall section and a cylindrical tube segment projecting from said wall section and defining a tubular passageway in communication therewith, comprising
a first sleeve portion dimensioned to be slidably received at one end within said tube segment;
a second sleeve portion dimensioned to be slidably received at one end over said tube segment;
said sleeve portions being concentric and joined at their other ends to form an annular recess for slidably receiving said tube segment in pressure sealing engagement; and
a grippable handle portion including a side wall portion extending in an axial direction from the other ends of said sleeve portions and a transverse end wall portion extending across the end thereof, said handle portion defining in conjunction with said first sleeve portion a chamber in pressure communication with said tubular passageway when said protector cap is inserted on the end of said tube segment, said sidewall being radially-inwardly compressible by opposing applied external forces to reduce the volume of said chamber upon insertion of said protector cap to form a partial vacuum within said chamber.

2. A protector cap as defined in claim 1 wherein the portion of said chamber within said handle portion is of substantially greater volume than the portion of said chamber within said first sleeve portion.

3. A protector cap as defined in claim 1 wherein said sidewall portion is sleeve shaped and generally identical in cross section to said first sleeve portion.

4. A protector cap as defined in claim 1 wherein said sidewall portion is sleeve shaped and generally identical in cross section to said second sleeve portion.

5. A container for injectable fluids comprising:
a housing forming a sealed container for said fluids having a puncturable wall section;
a cylindrical tube segment projecting from said wall section and defining a passageway in communication therewith; and
a removable protector cap including a first sleeve portion dimensioned to be slidably received at one end within said tube segment,
a second sleeve portion dimensioned to be slidably received at one end over said tube segment,
said sleeve portions being concentric and joined at their other ends to form an annular recess for slidably receiving said tube segment in pressure-sealing engagement, and
a grippable handle portion including a side wall portion extending in an axial direction from the other ends of said sleeve portions and a transverse end wall portion extending across the end thereof, said handle portion defining in conjunction with said first sleeve portion a chamber in pressure communication with said tubular passageway when said protector cap is inserted on the end of said tube segment, said sidewall being radially-inwardly compressible by the opposing applied external forces to reduce the volume of said chamber upon insertion of said protector cap to form a partial vacuum within said chamber.

6. A protector cap as defined in claim 5 wherein the portion of said chamber within said handle portion is of substantially greater volume than the portion of said chamber within said first sleeve portion.

7. A protector cap as defined in claim 5 wherein said sidewall portion is sleeve shaped and generally identical in cross sections to said first sleeve portion.

8. A protector cap as defined in claim 6 wherein said sidewall portion is sleeve shaped and generally identical in cross section to said second sleeve portion.

* * * * *